United States Patent
Jia et al.

(10) Patent No.: US 12,264,310 B1
(45) Date of Patent: Apr. 1, 2025

(54) INTRACELLULAR RADIATION MICRODOSIMETRIC DETECTION STRUCTURE AND DETECTION METHOD

(71) Applicant: SHANDONG UNIVERSITY, Weihai (CN)

(72) Inventors: Xianghong Jia, Weihai (CN); Pengzhi He, Weihai (CN); Chenyao Han, Weihai (CN); Quanqi Shi, Weihai (CN); Xiaoli Wang, Weihai (CN); Xiaoyan Gao, Weihai (CN); Shuai Wang, Weihai (CN); Shucheng Shi, Weihai (CN); Weiming Li, Weihai (CN)

(73) Assignee: SHANDONG UNIVERSITY, Weihai (CN)

( * ) Notice: Subject to any disclaimer, the term of this patent is extended or adjusted under 35 U.S.C. 154(b) by 0 days.

(21) Appl. No.: 18/950,326

(22) Filed: Nov. 18, 2024

(30) Foreign Application Priority Data

Dec. 26, 2023 (CN) .......................... 202311798429.5

(51) Int. Cl.
- *G01T 1/02* (2006.01)
- *C12M 1/34* (2006.01)
(Continued)

(52) U.S. Cl.
CPC ............. *C12N 15/01* (2013.01); *C12M 35/08* (2013.01); *C12M 41/30* (2013.01); *G01T 1/026* (2013.01); *G01T 7/00* (2013.01)

(58) Field of Classification Search
CPC ....... C12N 15/01; C12M 35/08; C12M 41/30; G01T 1/026; G01T 7/00
See application file for complete search history.

(56) References Cited

U.S. PATENT DOCUMENTS

| | | | | |
|---|---|---|---|---|
| 4,859,853 A | * | 8/1989 | Kronenberg | ............ G01T 1/026 250/370.07 |
| 2006/0012793 A1 | * | 1/2006 | Harris | .................. G01N 21/552 356/436 |

(Continued)

FOREIGN PATENT DOCUMENTS

| CN | 107505251 A | 12/2017 |
|---|---|---|
| CN | 109254018 A | 1/2019 |

(Continued)

OTHER PUBLICATIONS

Vu et al., "Performance of an Integrated Microfluidic Chip and Position Sensitive APD for the Detection of Beta Emitting Probes in Cell Cultures," IEEE Nuclear science symposium conference record, vol. M20-5, pp. 4057-4061. (Year: 2007).*

(Continued)

*Primary Examiner* — Kiho Kim
(74) *Attorney, Agent, or Firm* — IPRO, PLLC

(57) ABSTRACT

The present invention provides an intracellular radiation microdosimetric detection structure and detection method, and relates to the field of radiation microdosimetric detection technologies. The detection structure includes a first semiconductor detector unit, a first pixel array detector, a cellular microfluidic chip, a second pixel array detector, and a second semiconductor detector unit that are sequentially arranged in layers. The cellular microfluidic chip is configured for cell fixation and culture. The first semiconductor detector unit and the second semiconductor detector unit form a charged particle energy information detector combination for detecting deposit energy of charged particles in a semiconductor detector. The first pixel array detector and the second pixel array detector form a charged particle flux and position information detector combination for measuring a (Continued)

flux and an angle of charged particles incident at a position of the cellular microfluidic chip.

10 Claims, 6 Drawing Sheets

(51) Int. Cl.
*C12M 1/42* (2006.01)
*C12N 15/01* (2006.01)
*G01T 7/00* (2006.01)

(56) References Cited

U.S. PATENT DOCUMENTS

| | | | |
|---|---|---|---|
| 2008/0058991 A1* | 3/2008 | Lee | F16K 99/0001 |
| | | | 700/282 |
| 2009/0103091 A1* | 4/2009 | Jones | G01N 21/45 |
| | | | 356/342 |
| 2011/0036988 A1* | 2/2011 | Campbell | G01T 1/026 |
| | | | 250/370.07 |
| 2011/0051901 A1* | 3/2011 | Michel | G01T 1/366 |
| | | | 378/165 |
| 2012/0015376 A1* | 1/2012 | Bornhop | G01N 21/45 |
| | | | 435/7.1 |
| 2014/0170690 A1* | 6/2014 | Ziegler | H10F 39/011 |
| | | | 435/287.1 |
| 2016/0139021 A1* | 5/2016 | Stroock | G01N 33/246 |
| | | | 73/73 |
| 2019/0001327 A1* | 1/2019 | Wu | C12Q 1/6837 |

FOREIGN PATENT DOCUMENTS

| | | |
|---|---|---|
| CN | 111983667 A | 11/2020 |
| CN | 114428084 A | 5/2022 |
| CN | 115804917 A | 3/2023 |
| CN | 115877433 A | 3/2023 |
| WO | 02059365 A1 | 8/2002 |
| WO | 2022253920 A1 | 12/2022 |

OTHER PUBLICATIONS

Yan, Xuewen et al. "Research status and prospects of microdose experimentalmeasurement technology based on SOI" Radiation Protectation, vol. 42, No. 1, Jan. 2022.

* cited by examiner

INTRACELLULAR RADIATION MICRODOSIMETRIC DETECTION STRUCTURE AND DETECTION METHOD

TECHNICAL FIELD

The present invention relates to the field of radiation microdosimetric detection technologies, and in particular, to an intracellular radiation microdosimetric detection structure and detection method.

BACKGROUND OF THE INVENTION

The statements in this part provide only the background related to the present invention, but do not necessarily constitute the related art.

Biological effects caused by radiation from charged particles mainly include damage to cells and tissues, mutation of genetic materials, cell death, tumor formation, and the like. The quantities common for radiation protection, such as an absorbed dose and a dose equivalent, are average quantities, whereas deposit energy of charged particles in matter is inhomogeneous. Therefore, the concept of microdosimetry was proposed many years ago, using the quantities common for microdosimetry, such as specific energy and linear energy, to describe the inhomogeneity of energy deposition, which is more suitable for the study of biological effects in the case of low-dose radiation.

However, it is found from existing low-dose radiation studies that the biological effects exhibit diversity, including non-target effects such as bystander effects, abscopal effects, and genomic instability effects, and that particles from a charged particle beam source (which may be, but is not limited to, a charged particle accelerator) have specific dispersion on a micrometer scale, leading to different fluxes of particles that irradiate cells, making it impossible to achieve accurate measurement on a single-cell scale. In addition, physical average quantities are used for detection in the existing intracellular radiation microdosimetry, which has less accurate detection results, and consequently is not applicable to high-precision detection of low-dose radiation.

SUMMARY OF THE INVENTION

To resolve the deficiencies in the related art, the present invention provides an intracellular radiation microdosimetric detection structure and detection method, achieving microdosimetric measurements on a single-cell scale, which can obtain more accurate intracellular radiation microdosimetric data.

To achieve the foregoing objective, the present invention provides the following technical solutions:

According to a first aspect, the present invention provides an intracellular radiation microdosimetric detection structure.

The intracellular radiation microdosimetric detection structure, including a first semiconductor detector unit, a first pixel array detector, a cellular microfluidic chip, a second pixel array detector, and a second semiconductor detector unit that are sequentially arranged in layers, where the cellular microfluidic chip is configured for cell fixation and culture;

the first semiconductor detector unit and the second semiconductor detector unit form a charged particle energy information detector combination for detecting deposit energy of charged particles in a semiconductor detector; and the first pixel array detector and the second pixel array detector form a charged particle flux and position information detector combination for measuring a flux and an angle of charged particles incident at a position of the cellular microfluidic chip.

As a further limitation on the first aspect of the present invention, the first pixel array detector and the second pixel array detector have the same quantity and size of pixels, and the pixels of the first pixel array detector and the pixels of the second pixel array detector are arranged in a one-to-one correspondence; and cell culture chambers of the cellular microfluidic chip and the pixels of the first pixel array detector have the same quantity and are arranged in a one-to-one correspondence, and the cell culture chambers of the cellular microfluidic chip and the pixels of the second pixel array detector have the same quantity and are arranged in a one-to-one correspondence.

As a further limitation on the first aspect of the present invention, the first semiconductor detector unit and the second semiconductor detector unit have the same area and thickness, and an area of each semiconductor detector unit in the charged particle energy information detector combination is greater than or equal to an area of each pixel array detector in the charged particle flux and position information detector combination.

As a further limitation on the first aspect of the present invention, the first pixel array detector and the second pixel array detector have the same thickness, quantity of pixels, and area of a pixel, and an area of a single cell culture chamber of the cellular microfluidic chip is greater than or equal to an area of a single pixel of the first pixel array detector and the second pixel array detector in the charged particle flux and position detector combination; and the first semiconductor detector unit, the first pixel array detector, the cellular microfluidic chip, the second pixel array detector, and the second semiconductor detector unit are coaxially arranged in parallel.

According to a second aspect, the present invention provides an intracellular radiation microdosimetric detection method.

Using the intracellular radiation microdosimetric detection structure according to the first aspect of the present invention, the intracellular radiation microdosimetric detection method includes the following processes:

placing the intracellular radiation microdosimetric detection structure in a radiation environment with a known type of charged particles, to obtain deposit energy of the charged particles in the first semiconductor detector unit and deposit energy of the charged particles in the second semiconductor detector unit respectively when the first semiconductor detector unit and the second semiconductor detector unit generate effective signals;

placing the intracellular radiation microdosimetric detection structure in the radiation environment with the known type of charged particles, to obtain position information of the charged particles that arrive at the first pixel array detector and the second pixel array detector;

performing a connection based on the obtained position information of the charged particles that arrive at the first pixel array detector and the second pixel array detector, to obtain a charged particle incidence angle and information about a position of a cell penetrated by the charged particles in the cellular microfluidic chip between the first pixel array detector and the second pixel array detector;

performing an inverse calculation based on the deposit energy of the charged particles in the first semiconductor detector unit, the deposit energy of the charged particles in the second semiconductor detector unit, and the obtained charged particle incidence angle, to obtain incident energy of the charged particles;

performing simulation and calculation based on the incident energy of the charged particles, the charged particle incidence angle, and the information about the position of the cell penetrated by the charged particles in the cellular microfluidic chip, to obtain deposit energy in the cell at the position;

calculating a track length of the charged particles in the cell based on the obtained charged particle incidence angle; and performing calculation based on the obtained deposit energy in the single cell at the position and the track length of the charged particles in the cell, to obtain linear energy and specific energy in the single cell at the position.

As a further limitation on the second aspect of the present invention, the performing the connection based on the position information of the charged particles that arrive at the first pixel array detector and the second pixel array detector, to obtain the charged particle incidence angle, including:

projecting a pixel position of the charged particles that arrive at the first pixel array detector onto the second pixel array detector, to obtain a distance $d_1$ between a projection position and a pixel position of the charged particles that arrive at the second pixel array detector; and obtaining a ratio of $d_1$ to a distance $d_2$ between the first pixel array detector and the second pixel array detector as a tangent value of an angle between an incident direction of the charged particles and a plane on which the first pixel array detector is located, where the angle between the incident direction of the charged particles and the plane on which the first pixel array detector is located is the charged particle incidence angle, which is arctan $(d_1/d_2)$.

As a further limitation on the second aspect of the present invention, the performing the inverse calculation based on the deposit energy of the charged particles in the first semiconductor detector unit, the deposit energy of the charged particles in the second semiconductor detector unit, and the charged particle incidence angle, to obtain the incident energy of the charged particles, including:

simulating a case in which charged particles of a known type with different energies are incident into the intracellular radiation microdosimetric detection structure according to the obtained charged particle incidence angle, to obtain a correspondence among incident particle energy of the charged particles, deposit energy of the particles in the first semiconductor detector unit, and deposit energy of the particles in the second semiconductor detector unit; and using the actually obtained deposit energy of the charged particles in the first semiconductor detector unit and the actually obtained deposit energy of the charged particles in the second semiconductor detector unit according to the obtained correspondence among the incident particle energy of the charged particles, the deposit energy of the particles in the first semiconductor detector unit, and the deposit energy of the particles in the second semiconductor detector unit, to obtain the incident particle energy of the charged particles.

As a further limitation on the second aspect of the present invention, the calculation is performed based on the track length of the charged particles in the cell at the position and the deposit energy of the charged particles in the cell at the position, to obtain the linear energy in the cell at the position, including:

calculating a ratio of the deposit energy in the cell at the position to the track length of the charged particles in the cell at the position, to obtain the linear energy in the cell at the position.

As a further limitation on the second aspect of the present invention, the calculation is performed based on the track length of the charged particles in the cell at the position and the deposit energy of the charged particles in the cell at the position, to obtain the specific energy in the cell at the position, including:

calculating a ratio of the deposit energy in the cell at the position to mass of the single cell, to obtain the specific energy in the cell at the position.

According to a third aspect, the present invention provides an intracellular radiation microdosimetric detection method.

Using the intracellular radiation microdosimetric detection structure according to the first aspect of the present invention, when the intracellular radiation microdosimetric detection structure is placed orthogonally to a charged particle beam, the intracellular radiation microdosimetric detection method includes the following processes:

detecting deposit energy of charged particles in a detector by the first semiconductor detector unit and the second semiconductor detector unit, to obtain incident energy of the charged particles;

detecting a flux of the charged particles in a single pixel by the first pixel array detector and the second pixel array detector as a flux of the charged particles incident into a cell in a culture chamber of the cellular microfluidic chip at a position corresponding to the pixel; and performing simulation and calculation based on the incident energy of the charged particles and the flux of the charged particles incident into the single cell, to obtain a deposit microdose in the single cell.

Compared with the related art, the present invention has the following beneficial effects:

(1) The present invention creatively develops an intracellular radiation microdosimetric detection structure including a first semiconductor detector unit, a first pixel array detector, a cellular microfluidic chip, a second pixel array detector, and a second semiconductor detector unit that are sequentially arranged in layers, which can achieve microdosimetric measurements on a single-cell scale and obtain more accurate data with higher reliability. In addition, the structure is very compact and occupies less space, which can be used in miniaturized low-power-consumption devices.

(2) The present invention creatively provides an intracellular radiation microdosimetric detection method. Calculation is performed based on obtained deposit energy in a single cell at a position and a track length of charged particles in the cell, to obtain linear energy and specific energy in the single cell at the position, which can obtain an intracellular radiation microdose more accurately, improving the accuracy of measurements of microdosimetric data such as linear energy and specific energy.

Some of advantages of the additional aspects of the present invention are given in the following description, and some become apparent from the following description or are learned through practice of the present invention.

BRIEF DESCRIPTION OF THE DRAWINGS

The accompanying drawings of this specification that constitute a part of the present invention are used to provide a further understanding of the present invention. Exemplary embodiments of the present invention and descriptions thereof are used to explain the present invention, and do not constitute any inappropriate limitation to the present invention.

Figure 1:
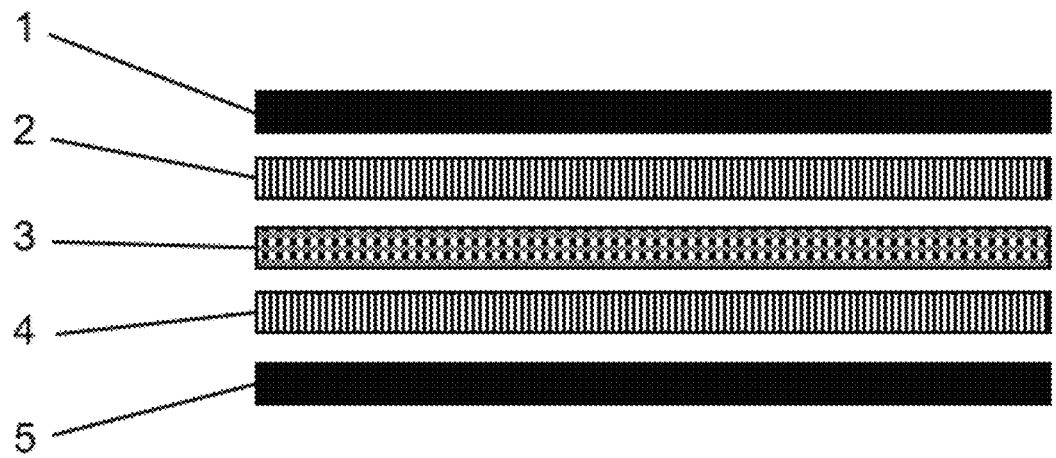
FIG. 1 is a structural block diagram of an intracellular radiation microdosimetric detection structure according to Embodiment 1 of the present invention.
Figure 2:
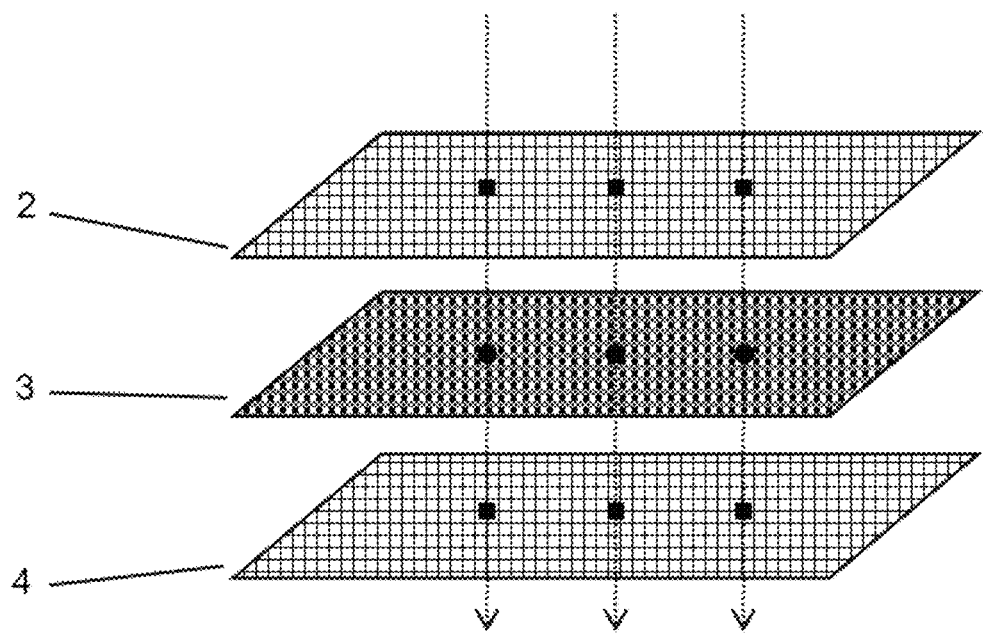
FIG. 2 is a schematic diagram of vertical incidence of charged particles to sequentially pass through a first pixel array detector, a cellular microfluidic chip, and a second pixel array detector according to Embodiment 2 of the present invention.
Figure 3:
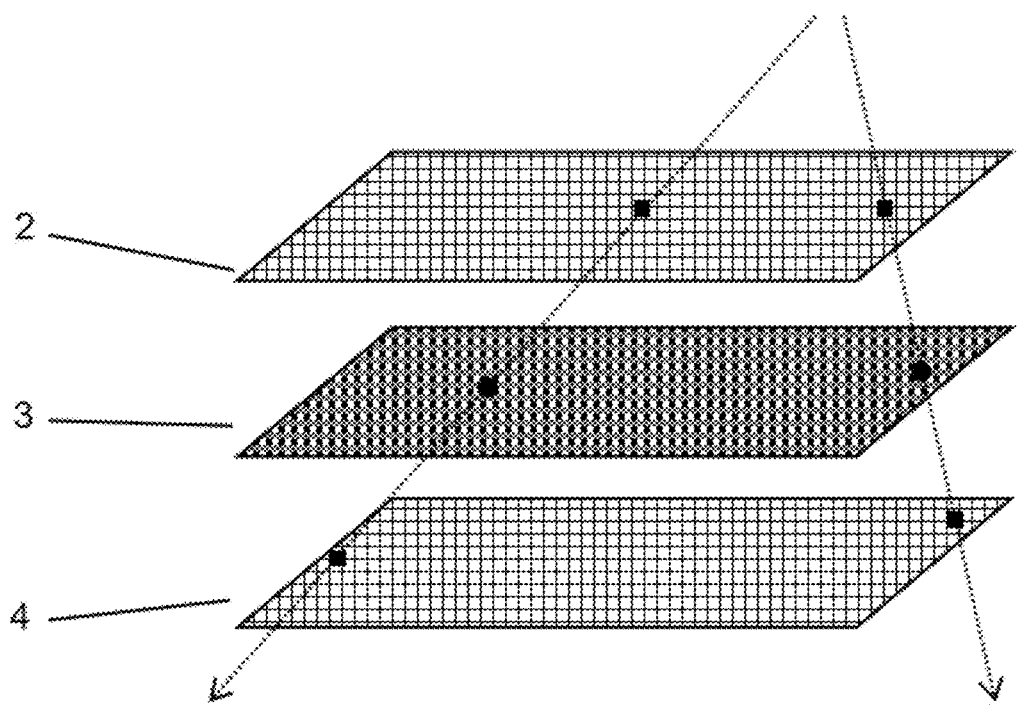
FIG. 3 is a schematic diagram of oblique incidence of charged particles to sequentially pass through a first pixel array detector, a cellular microfluidic chip, and a second pixel array detector according to Embodiment 2 of the present invention.
Figure 4:
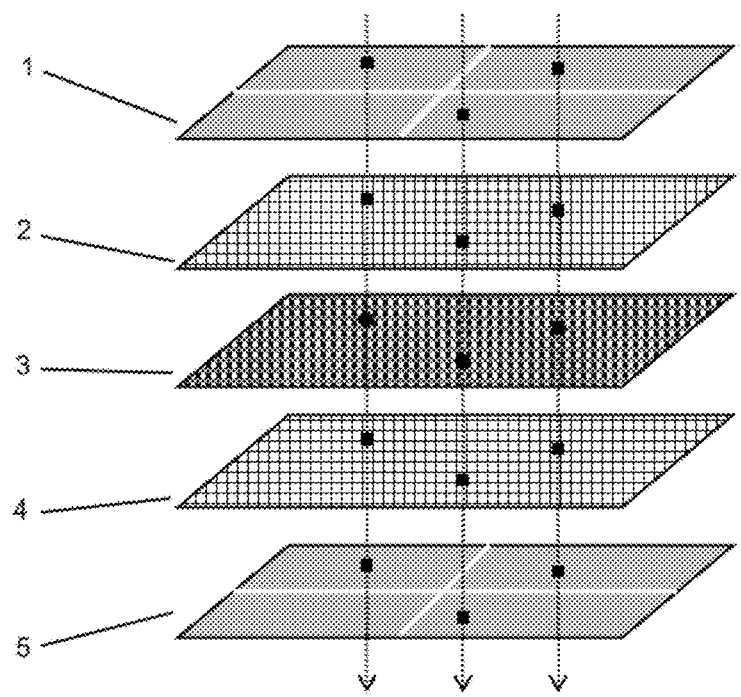
FIG. 4 is a schematic diagram of vertical incidence of charged particles to sequentially pass through a first semiconductor detector unit, a first pixel array detector, a cellular microfluidic chip, a second pixel array detector, and a second semiconductor detector unit when each of the first semiconductor detector unit and the second semiconductor detector unit includes four semiconductor detectors according to Embodiment 2 of the present invention, where the semiconductor detector unit can assist in determining an incident direction of the charged particles and a position of a cell penetrated by the charged particles.
Figure 5:
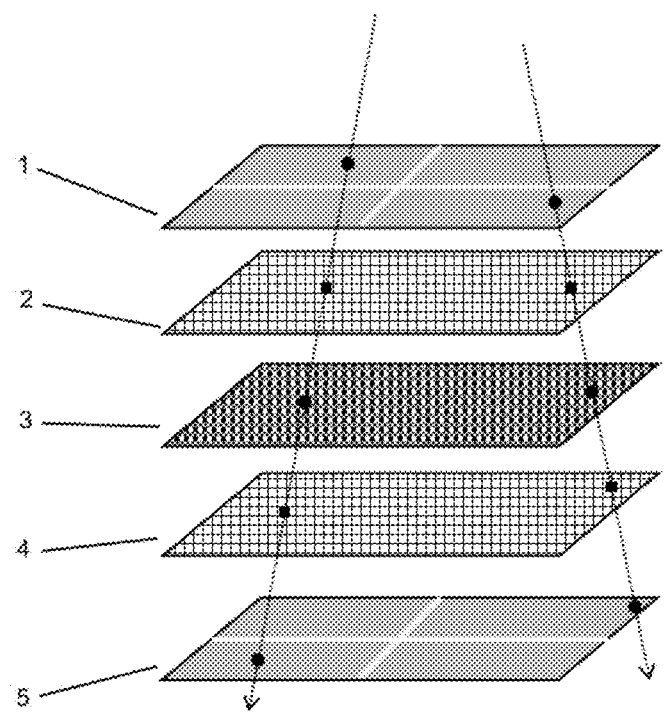
FIG. 5 is a schematic diagram of oblique incidence of charged particles to sequentially pass through a first semiconductor detector unit, a first pixel array detector, a cellular microfluidic chip, a second pixel array detector, and a second semiconductor detector unit when each of the first semiconductor detector unit and the second semiconductor detector unit includes four semiconductor detectors according to Embodiment 2 of the present invention, where the semiconductor detector unit can assist in determining an incident direction of the charged particles and a position of a cell penetrated by the charged particles.
Figure 6:
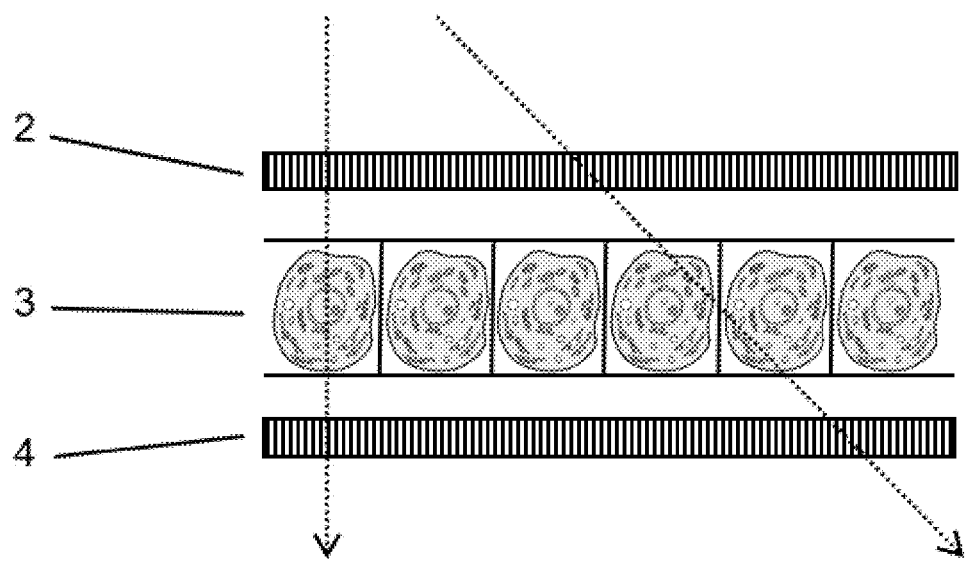
FIG. 6 is a schematic diagram of vertical incidence or oblique incidence of charged particles to sequentially pass through a first pixel array detector, a cellular microfluidic chip, and a second pixel array detector to obtain a track length of the charged particles in a cell according to Embodiment 2 of the present invention.

In the drawings: 1, first semiconductor detector unit; 2, first pixel array detector; 3, cellular microfluidic chip; 4, second pixel array detector; 5, second semiconductor detector unit.

DETAILED DESCRIPTION OF THE INVENTION

The following further describes the present invention with reference to the accompanying drawings and the embodiments.

It should be noted that the following detailed descriptions are all exemplary and are intended to provide further descriptions of the present invention. Unless otherwise indicated, all technical and scientific terms used herein have the same meaning as would normally be understood by a person of ordinary skill in the art of the present invention.

The embodiments in the present invention and features in the embodiments may be mutually combined in the case of no conflict.

Embodiment 1

As shown in FIG. 1, the present embodiment provides an intracellular radiation microdosimetric detection structure, including: a first semiconductor detector unit 1, a first pixel array detector 2, a cellular microfluidic chip 3, a second pixel array detector 4, and a second semiconductor detector unit 5 that are sequentially arranged in layers.

In the present embodiment, preferably, each semiconductor detector unit includes at least one semiconductor detector, all pixel array detectors have a consistent quantity and size of pixels, and a quantity and area of cell culture chambers of the cellular microfluidic chip are consistent with a quantity and area of pixels of a neighboring pixel array detector.

The first semiconductor detector unit 1 and the second semiconductor detector unit 5 forms a charged particle energy information detector combination for detecting deposit energy of charged particles incident into the detection structure, to obtain incident energy of the charged particles through an inverse calculation.

The first pixel array detector 2 and the second pixel array detector 4 form a charged particle flux and position information detector combination for detecting flux (quantity) and position information of charged particles incident into the detection structure.

The cellular microfluidic chip 3 is arranged between the first pixel array detector 2 and the second pixel array detector 4 for cell fixation and culture.

It is to be noted that, in the present embodiment, each semiconductor detector operates independently to record deposit energy separately, and there may be one or more semiconductor detectors in each semiconductor detector unit. This can assist the pixel array detector in determining position information of charged particles, specifically depending on an actual requirement.

Optionally, in some specific implementations, the first semiconductor detector unit 1 and the second semiconductor detector unit 5 forms a charged particle energy information detector combination, and the first semiconductor detector unit 1 and the second semiconductor detector unit 5 have the same area and thickness.

Optionally, in some specific implementations, the first pixel array detector 2 and the second pixel array detector 4 form a charged particle flux and position information detector combination, and the first pixel array detector 2 and the second pixel array detector 4 have the same thickness, quantity of pixels, and area of a pixel.

Optionally, in some specific implementations, to increase detection efficiency, an area of a detector in the charged particle energy information detector combination may be greater than or equal to an area of a detector in the charged particle flux and position information detector combination.

Optionally, in some specific implementations, an area of a cell culture chamber in the cellular microfluidic chip 3 is greater than or equal to an area of a single pixel of a detector in the charged particle flux and position information detector combination.

Optionally, in some specific implementations, the semiconductor detector unit, the pixel array detector, and the cellular microfluidic chip are coaxially arranged in parallel. It is to be noted that the semiconductor detector unit, the pixel array detector, and the cellular microfluidic chip may be arranged based on the size of the space of the actual detection structure in any way but in the fixed sequence.

With the special structural design of the intracellular radiation microdosimetric detection structure of the present invention, the incident energy and incident angle of charged particles incident into a single cell, and the incident flux of charged particles in a particular case are effectively obtained.

Embodiment 2 The present embodiment further provides an intracellular radiation microdose obtaining method, as shown in FIGS. 2 to 6, using the intracellular radiation microdosimetric detection structure in Embodiment 1. The method includes the following processes:

S1: To ensure data validity, it is necessary to ensure that charged particles pass through five structural modules, that is, generate signals in the first semiconductor detector unit 1, the first pixel array detector 2, the second pixel array detector 4, and the second semiconductor detector unit 5. The intracellular radiation microdosimetric detection structure is placed in a radiation environment with a known type of charged particles, to obtain deposit energy of the charged particles in the first semiconductor detector unit 1 and deposit energy of the charged particles in the second semiconductor detector unit 5 respectively when the first semiconductor detector unit 1 and the second semiconductor detector unit 5 generate effective signals.

S2: The intracellular radiation microdosimetric detection structure is placed in the radiation environment with the known type of charged particles in S1, to obtain position information of the charged particles that arrive at the first pixel array detector 2 and the second pixel array detector 4.

S3: A connection is performed based on the position information of the charged particles that arrive at the first pixel array detector 2 and the second pixel array detector 4 obtained in step S2, to obtain a charged particle incidence angle and information about a position of a cell penetrated by the charged particles in the cellular microfluidic chip between the first pixel array detector 2 and the second pixel array detector 4.

S4: An inverse calculation is performed based on the deposit energy of the charged particles in the first semiconductor detector unit 1 and the deposit energy of the charged particles in the second semiconductor detector unit 5 that are obtained in step S1, and the charged particle incidence angle obtained in step S3, to obtain incident energy of the charged particles.

S5: Simulation and calculation are performed based on the incident energy of the charged particles obtained in step S4, the charged particle incidence angle obtained in step S3, and the information about the position of the cell penetrated by the charged particles in the cellular microfluidic chip obtained in step S3, to obtain deposit energy in the cell at the position.

S6: A track length of the charged particles in the cell is calculated based on the charged particle incidence angle obtained in step S3.

S7: Calculation is performed based on the deposit energy in the single cell at the position obtained in step S5 and the track length of the charged particles in the cell obtained in step S6, to obtain linear energy and specific energy in the single cell at the position.

In step S3, the connection is performed based on the position information of the charged particles that arrive at the first pixel array detector and the second pixel array detector to obtain the charged particle incidence angle specifically includes the following processes:

S3.1: A pixel position of the charged particles that arrive at the first pixel array detector is projected onto the second pixel array detector, to obtain a distance $d_1$ between a projection position and a pixel position of the charged particles that arrive at the second pixel array detector.

S3.2: A ratio of $d_1$ to a distance $d_2$ between the first pixel array detector and the second pixel array detector is obtained as a tangent value of an angle between an incident direction of the charged particles and a plane on which the first pixel array detector is located, where the angle between the incident direction of the charged particles and the plane on which the first pixel array detector is located is the charged particle incidence angle, which is $\arctan(d_1/d_2)$.

In step S4, the inverse calculation is performed based on the deposit energy of the charged particles in the first semiconductor detector unit, the deposit energy of the charged particles in the second semiconductor detector unit, and the charged particle incidence angle to obtain the incident energy of the charged particles specifically includes the following processes:

S4.1: A case in which charged particles of a known type with different energies are incident into the intracellular radiation microdosimetric detection structure according to the charged particle incidence angle obtained in step S3 is simulated by using a Monte Carlo simulation tool, for example, Geant4, to obtain a correspondence among incident particle energy of the charged particles, deposit energy of the particles in the first semiconductor detector unit, and deposit energy of the particles in the second semiconductor detector unit.

S4.2: The actually obtained deposit energy of the charged particles in the first semiconductor detector unit and the actually obtained deposit energy of the charged particles in the second semiconductor detector unit are used according to the correspondence among the incident particle energy of the charged particles, the deposit energy of the particles in the first semiconductor detector unit, and the deposit energy of the particles in the second semiconductor detector unit obtained in step S4.1, to obtain the incident particle energy of the charged particles.

In step S6, that the track length of the charged particles in the cell is calculated based on the charged particle incidence angle specifically includes the following processes:

S6.1: The charged particle incidence angle θ is obtained according to the method in S3.2.

S6.2: The track length $l=d_{cell}/\sin(\theta)$ of the charged particles in the cell is obtained based on the cell layer thickness d cell.

In step S7, that calculation is performed based on the track length of the charged particles in the cell at the position and the deposit energy of the charged particles in the cell at the position to obtain the linear energy in the cell at the position specifically includes:

calculating a ratio of the deposit energy in the cell at the position to the track length of the charged particles in the cell at the position, to obtain the linear energy in the cell at the position.

In step S7, that calculation is performed based on the track length of the charged particles in the cell at the position and the deposit energy of the charged particles in the cell at the position to obtain the specific energy in the cell at the position specifically includes:

calculating a ratio of the deposit energy in the cell at the position to mass of the single cell, to obtain the specific energy in the cell at the position.

More specifically, in some other implementations, there is a special case. When the intracellular radiation microdosimetric detection structure is placed orthogonally to a charged particle beam, the method includes the following processes:

(1) Deposit energy of charged particles in a detector is detected by the first semiconductor detector unit and the second semiconductor detector unit, to obtain incident energy of the charged particles.

(2) A flux of the charged particles in a single pixel is detected by the first pixel array detector and the second pixel array detector as a flux of the charged particles incident into a cell in a culture chamber of the cellular microfluidic chip at a position corresponding to the pixel.

(3) Simulation and calculation are performed based on the incident energy of the charged particles and the flux of the charged particles incident into the single cell, to obtain a deposit microdose in the single cell.

By the foregoing detection method in the present invention, an intracellular radiation microdose can be obtained more accurately, improving the accuracy of measurements of microdosimetric data such as linear energy and specific energy.

As it is difficult to obtain isotropic charged particles with a specific incident angle and specific energy distribution in actual experiments, in the following, isotropic charged particles of a known type with a specific incident angle and specific energy distribution are simulated by using the Geant4 simulation software. Then, the charged particles are detected by using the intracellular radiation microdosimetric detection structure and obtaining method in the present invention, to verify the validity.

In the present embodiment, both the first semiconductor detector unit 1 and the second semiconductor detector unit 5 are a piece of square silicon detector with a thickness of 500 μm and a side length of 50 mm; both the first pixel array detector 2 and the second pixel array detector 4 are a piece of square silicon detector with a thickness of 700 μm and a side length of 50 mm; the cellular microfluidic chip is provided to be a square with a thickness of 10 μm and a side length of 50 mm; and adjacent structures are spaced 1 mm apart, a culture chamber of the cellular microfluidic chip is filled with a cell, and component density is set to cytoplasmic density of 1.00 g/cm$^3$, which is the same as that of water.

Figure 7:
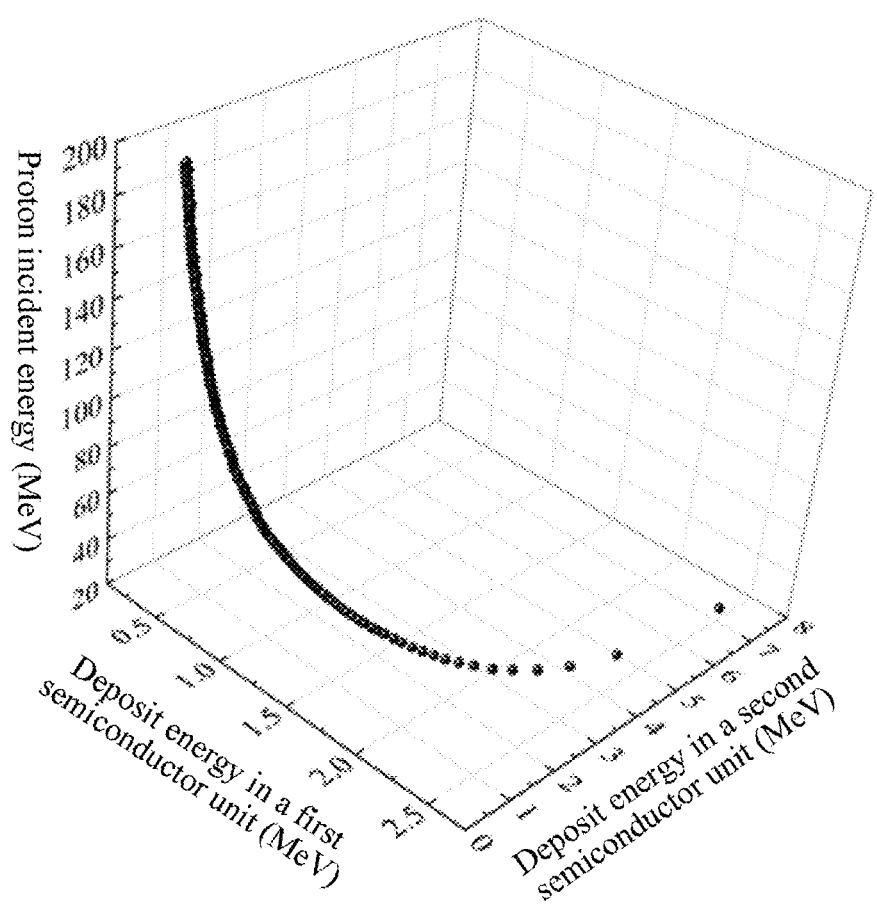
FIG. 7 is a schematic diagram of results of simulation using Geant4 according to Embodiment 2 of the present invention, where protons with different energies are incident vertically and sequentially pass through five layers of structures, and generate deposit energy in a semiconductor unit, and an inverse calculation may be performed based on a combination of deposit energy in a first semiconductor detector unit and deposit energy in a second semiconductor detector unit to obtain unique proton incident energy (Proton IN Energy)

Vertical incidence of protons with different energies is simulated using Geant4 to sequentially pass through five layers of structures, to generate deposit energy in a semiconductor unit. Similarly, the inverse calculation may be performed based on a combination of the deposit energy in the first semiconductor detector unit and the deposit energy in the second semiconductor detector unit to obtain unique proton incident energy (Proton IN Energy), as shown in FIG. 7.

Figure 8:
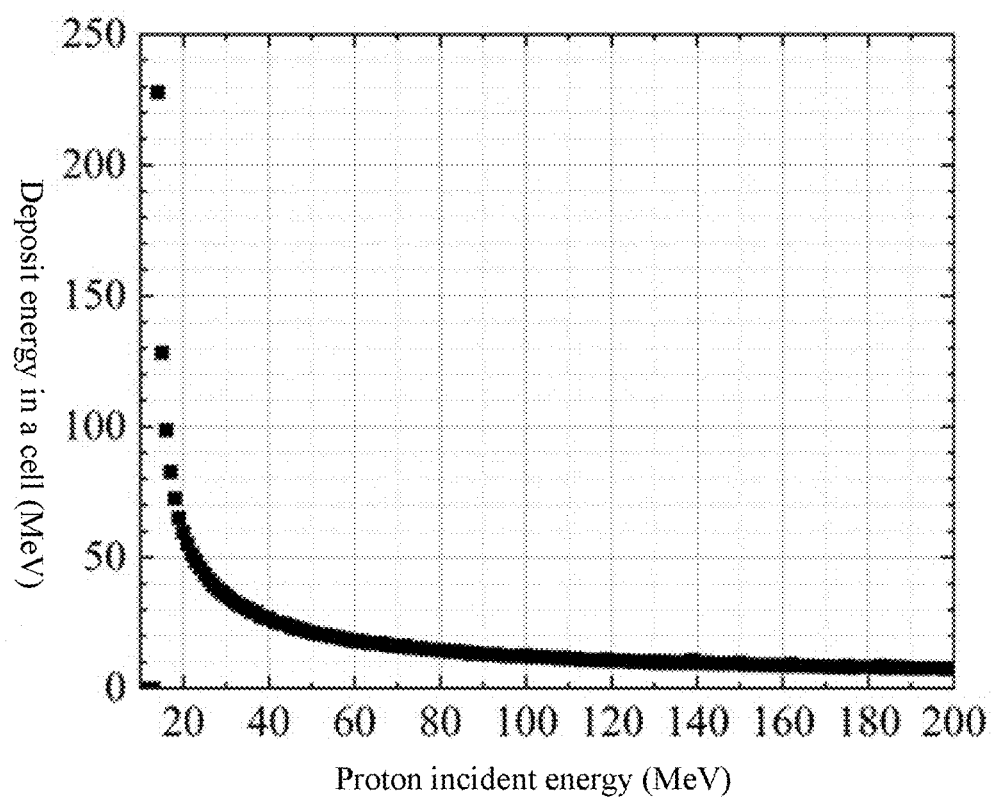
FIG. 8 is a schematic diagram of results of simulation using Geant4 according to Embodiment 2 of the present invention, where protons with different energies (0-200 MeV) are incident vertically and sequentially pass through five layers of structures, and generate deposit energy in a cell (Deposit Energy in cell) in a chamber of a microfluidic chip.

(1) When charged particles (for example, protons) are vertically incident into the intracellular radiation microdosimetric detection structure designed in the present invention, deposit energy in a cell (Deposit Energy in cell) in a chamber of the microfluidic chip may be obtained based on the obtained proton incident energy according to results of simulation of Geant4, as shown in FIG. 8.

Microdosimetric linear energy and specific energy may be obtained through calculation based on the deposit energy in the cell, a diameter of the cell (or a thickness of the microfluidic chip), and mass of the cell.

Figure 9:
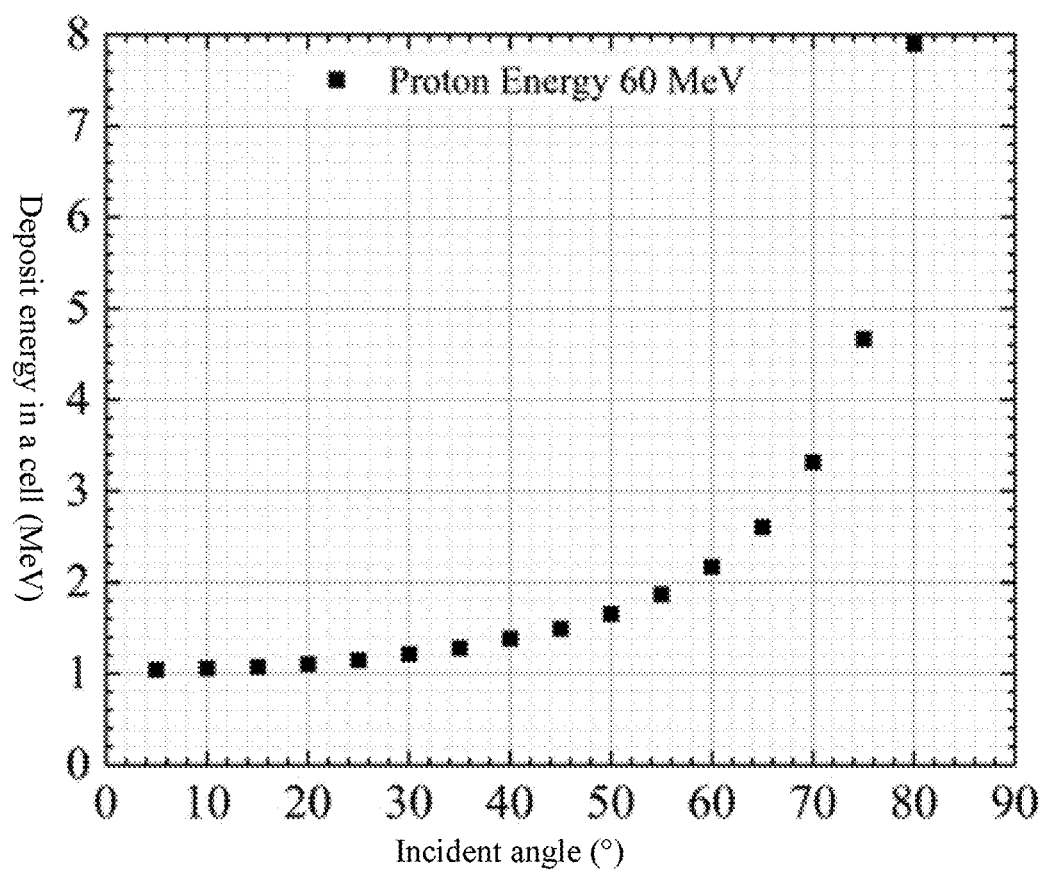
FIG. 9 is a schematic diagram of results of simulation using Geant4 according to Embodiment 2 of the present invention, where protons with an energy of 60 MeV are incident from different angles and sequentially pass through five layers of structures, with vertical incidence at 0°, and generate deposit energy in a cell (Deposit Energy in cell) in a chamber of a microfluidic chip.

(2) When charged particles (for example, protons) are obliquely incident into the intracellular radiation microdosimetric detection structure designed in the present invention, an oblique angle of the protons in an incident direction is obtained based on a particle track obtained by the pixel array detector, and deposit energy in a cell (Deposit Energy in cell) in a chamber of the microfluidic chip may be obtained according to results of simulation of Geant4 based on the proton incident energy obtained through the inverse calculation by the first semiconductor detector unit and the second semiconductor detector unit, as shown in FIG. 9.

Microdosimetric linear energy and specific energy may be obtained separately through calculation based on the deposit energy in the cell, the oblique angle of the particles in the incident direction, a track length of the particles traversing the cell, and mass of the cell.

The foregoing descriptions are merely preferred embodiments of the present invention and are not intended to limit the present invention. A person skilled in the art may make various modifications and changes of the present invention. Any modification, equivalent replacement, or improvement made within the spirit and principle of the present invention shall fall within the protection scope of the present invention.

The invention claimed is:

1. An intracellular radiation microdosimetric detection structure, comprising:

a first semiconductor detector unit, a first pixel array detector, a cellular microfluidic chip, a second pixel array detector, and a second semiconductor detector unit that are sequentially arranged in layers, wherein the cellular microfluidic chip is configured for cell fixation and culture;

the first semiconductor detector unit and the second semiconductor detector unit form a charged particle energy information detector combination for detecting deposit energy of charged particles in a semiconductor detector; and the first pixel array detector and the second pixel array detector form a charged particle flux and position information detector combination for measuring a flux and an angle of charged particles incident at a position of the cellular microfluidic chip.

2. The intracellular radiation microdosimetric detection structure according to claim 1, wherein quantity and size of pixels of the first pixel array detector are equal to quantity and size of pixels of the second pixel array detector, and the pixels of the first pixel array detector and the pixels of the second pixel array detector are arranged in a one-to-one correspondence; and quantity of cell culture chambers of the cellular microfluidic chip is equal to the quantity of the pixels of the first pixel array detector or the quantity of the pixels of the second pixel array detector, and the cell culture chambers of the cellular microfluidic chip and the pixels of the first pixel array detector or the pixels of the second pixel array detector are arranged in a one-to-one correspondence.

3. The intracellular radiation microdosimetric detection structure according to claim 1, wherein an area and thickness of the first semiconductor detector unit are equal to an area and thickness of the second semiconductor detector unit, and the area of the first and the second semiconductor detector unit in the charged particle energy information detector combination is greater than or equal to an area of the first and the second pixel array detector in the charged particle flux and position information detector combination.

4. The intracellular radiation microdosimetric detection structure according to claim 1, wherein a thickness and an area of a single pixel of the first pixel array detector are equal to a thickness and an area of a single pixel of the second pixel array detector, and an area of a single cell culture chamber of the cellular microfluidic chip is greater than or equal to the area of the single pixel of the first pixel array detector and the second pixel array detector in the charged particle flux and position information detector combination; and the first semiconductor detector unit, the first pixel array detector, the cellular microfluidic chip, the second pixel array detector, and the second semiconductor detector unit are coaxially arranged in parallel.

5. An intracellular radiation microdosimetric detection method, using the intracellular radiation microdosimetric detection structure according to claim 1, the method comprising the following processes:

placing the intracellular radiation microdosimetric detection structure in a radiation environment with a known type of charged particles, to obtain deposit energy of the charged particles in the first semiconductor detector unit and deposit energy of the charged particles in the second semiconductor detector unit respectively when the first semiconductor detector unit and the second semiconductor detector unit generate effective signals;

placing the intracellular radiation microdosimetric detection structure in the radiation environment with the known type of charged particles, to obtain position information of the charged particles that arrive at the first pixel array detector and the second pixel array detector;

performing a connection based on the obtained position information of the charged particles that arrive at the first pixel array detector and the second pixel array detector, to obtain a charged particle incidence angle and information about a position of a cell penetrated by the charged particles in the cellular microfluidic chip between the first pixel array detector and the second pixel array detector;

performing an inverse calculation based on the deposit energy of the charged particles in the first semiconductor detector unit, the deposit energy of the charged particles in the second semiconductor detector unit, and the obtained charged particle incidence angle, to obtain incident energy of the charged particles;

performing simulation and calculation based on the incident energy of the charged particles, the charged particle incidence angle, and the information about the position of the cell penetrated by the charged particles in the cellular microfluidic chip, to obtain deposit energy in the cell at the position;

calculating a track length of the charged particles in the cell based on the obtained charged particle incidence angle; and performing calculation based on the obtained deposit energy in the single cell at the position and the track length of the charged particles in the cell, to obtain linear energy and specific energy in the single cell at the position.

6. The intracellular radiation microdosimetric detection method according to claim 5, wherein the performing the connection based on the position information of the charged particles that arrive at the first pixel array detector and the second pixel array detector, to obtain the charged particle incidence angle, comprising:

projecting a pixel position of the charged particles that arrive at the first pixel array detector onto the second pixel array detector, to obtain a distance $d_1$ between a projection position and a pixel position of the charged particles that arrive at the second pixel array detector; and obtaining a ratio of $d_1$ to a distance $d_2$ between the first pixel array detector and the second pixel array detector as a tangent value of an angle between an incident direction of the charged particles and a plane on which the first pixel array detector is located, wherein the angle between the incident direction of the charged particles and the plane on which the first pixel array detector is located is the charged particle incidence angle, which is $\arctan(d_1/d_2)$.

7. The intracellular radiation microdosimetric detection method according to claim 5, wherein the performing the inverse calculation based on the deposit energy of the charged particles in the first semiconductor detector unit, the deposit energy of the charged particles in the second semiconductor detector unit, and the charged particle incidence angle, to obtain the incident energy of the charged particles, comprising:

simulating a case in which charged particles of a known type with different energies are incident into the intracellular radiation microdosimetric detection structure according to the obtained charged particle incidence angle, to obtain a correspondence among incident particle energy of the charged particles, deposit energy of the particles in the first semiconductor detector unit, and deposit energy of the particles in the second semiconductor detector unit; and using the actually obtained deposit energy of the charged particles in the first semiconductor detector unit and the actually obtained deposit energy of the charged particles in the second semiconductor detector unit according to the obtained correspondence among the incident particle energy of the charged particles, the deposit energy of the particles in the first semiconductor detector unit, and the deposit energy of the particles in the second semiconductor detector unit, to obtain the incident particle energy of the charged particles.

8. The intracellular radiation microdosimetric detection method according to claim 5, wherein the calculation is performed based on the track length of the charged particles in the cell at the position and the deposit energy of the charged particles in the cell at the position, to obtain the linear energy in the cell at the position, comprising:
  calculating a ratio of the deposit energy in the cell at the position to the track length of the charged particles in the cell at the position, to obtain the linear energy in the cell at the position.

9. The intracellular radiation microdosimetric detection method according to claim 5, wherein the calculation is performed based on the track length of the charged particles in the cell at the position and the deposit energy of the charged particles in the cell at the position, to obtain the specific energy in the cell at the position comprises:
  calculating a ratio of the deposit energy in the cell at the position to mass of the single cell, to obtain the specific energy in the cell at the position.

10. An intracellular radiation microdosimetric detection method, using the intracellular radiation microdosimetric detection structure according to claim 1, wherein when the intracellular radiation microdosimetric detection structure is placed orthogonally to a charged particle beam, the method comprises the following processes:
  detecting deposit energy of charged particles in a detector by the first semiconductor detector unit and the second semiconductor detector unit, to obtain incident energy of the charged particles;
  detecting a flux of the charged particles in a single pixel by the first pixel array detector and the second pixel array detector as a flux of the charged particles incident into a cell in a culture chamber of the cellular microfluidic chip at a position corresponding to the pixel; and
  performing simulation and calculation based on the incident energy of the charged particles and the flux of the charged particles incident into the single cell, to obtain a deposit microdose in the single cell.

* * * * *